US011207476B2

(12) United States Patent
Clements

(10) Patent No.: US 11,207,476 B2
(45) Date of Patent: *Dec. 28, 2021

(54) FLEXIBLE BAG SPACER DEVICE FOR AN INHALER

(71) Applicant: Inspiring Pty Ltd, Dalkeith (AU)

(72) Inventor: Barry Spencer Clements, Dalkeith (AU)

(73) Assignee: Inspiring Pty Ltd, Dalkeith (AU)

( * ) Notice: Subject to any disclaimer, the term of this patent is extended or adjusted under 35 U.S.C. 154(b) by 422 days.

This patent is subject to a terminal disclaimer.

(21) Appl. No.: 16/094,852

(22) PCT Filed: Apr. 18, 2017

(86) PCT No.: PCT/AU2017/050347
§ 371 (c)(1),
(2) Date: Oct. 18, 2018

(87) PCT Pub. No.: WO2017/181228
PCT Pub. Date: Oct. 26, 2017

(65) Prior Publication Data
US 2019/0125991 A1      May 2, 2019

(30) Foreign Application Priority Data

Apr. 18, 2016  (AU) ................ 2016901448

(51) Int. Cl.
*A61M 15/00*     (2006.01)
(52) U.S. Cl.
CPC .... *A61M 15/0086* (2013.01); *A61M 15/0021* (2014.02); *A61M 15/009* (2013.01);
(Continued)

(58) Field of Classification Search
CPC .......... A61M 15/0021; A61M 15/0086; A61M 15/0088; A61M 15/009; A61M 2205/0216; A61M 2205/0233
See application file for complete search history.

(56) References Cited

U.S. PATENT DOCUMENTS 2,705,954 A * 4/1955 Andrews ................ A62B 18/08
                                                         128/205.17
3,923,043 A * 12/1975 Yanda ..................... A61B 5/091
                                                         600/541
(Continued)

FOREIGN PATENT DOCUMENTS

| GB | 2285396 A * | 7/1995 | ........ A61M 15/0086 |
| WO | WO-1993/011817 A1 | 6/1993 | |
| WO | WO-0136032 A1 * | 5/2001 | ........ A61M 15/0088 |

OTHER PUBLICATIONS

Kilcullen, Shane; "International Search Report"; dated Jun. 26, 2017; 3 pages.

*Primary Examiner* — Kathryn E Ditmer
(74) *Attorney, Agent, or Firm* — Winstead PC

(57) ABSTRACT

The invention relates to a valveless spacer device for a metered dose inhaler (MDI), the spacer device comprising a body having an inlet and an outlet opposed from the inlet, a demountable, flexible bag attached to the body, the bag and body together defining a chamber, such that the inlet and outlet are in fluid flow communication with an interior of the chamber, wherein the inlet is configured to be connected to an MDI containing a drug to be inhaled and wherein the flexible bag, following actuation of the MDI, serves as a reservoir allowing for the formation of a cloud or mist of the drug therewithin which is then ready for inhalation, the flexible bag being configured to be at least partially deflatable and at least partially inflatable commensurate with a single breath and/or rebreathing.

14 Claims, 13 Drawing Sheets

(52) U.S. Cl.
CPC ............. *A61M 2202/064* (2013.01); *A61M 2205/0216* (2013.01); *A61M 2205/0233* (2013.01); *A61M 2205/59* (2013.01)

(56) References Cited

U.S. PATENT DOCUMENTS

| | | | | |
|---|---|---|---|---|
| 4,119,097 A * | 10/1978 | Spector | ............... | A62B 7/02 128/205.17 |
| 4,484,577 A * | 11/1984 | Sackner | ............... | A61K 9/0073 128/200.23 |
| 4,790,305 A * | 12/1988 | Zoltan | ............... | A61M 15/0086 128/200.23 |
| 5,020,530 A * | 6/1991 | Miller | ............... | A61M 15/00 128/200.21 |
| 5,318,016 A * | 6/1994 | Mecikalski | ...... | A61M 15/0086 128/200.14 |
| 5,613,489 A * | 3/1997 | Miller | ............... | A61M 15/0086 128/200.14 |
| 5,842,467 A * | 12/1998 | Greco | ............... | A61M 16/0078 128/200.23 |
| 6,158,428 A * | 12/2000 | Mecikalski | ...... | A61M 15/0086 128/200.23 |
| 6,390,090 B1 * | 5/2002 | Piper | ............... | A61M 15/0086 128/200.14 |
| 6,401,710 B1 * | 6/2002 | Scheuch | .......... | A61M 15/0086 128/200.21 |
| 6,463,929 B1 * | 10/2002 | Scheuch | .......... | A61M 15/0086 128/200.22 |
| 7,418,962 B1 | 9/2008 | Rao | | |
| 7,726,310 B2 * | 6/2010 | Andrus | ............ | A61M 15/0088 128/205.13 |
| 9,108,011 B2 * | 8/2015 | Wachtel | ............ | A61M 15/0086 |
| 2001/0035181 A1 * | 11/2001 | Elkins | ............... | A61M 15/0088 128/200.21 |
| 2002/0069870 A1 * | 6/2002 | Farmer | ............ | A61M 16/0833 128/200.22 |
| 2003/0041859 A1 * | 3/2003 | Abrams | ............ | A61M 16/101 128/200.22 |
| 2004/0234610 A1 * | 11/2004 | Hall | ............... | A61M 15/0088 424/489 |
| 2005/0217667 A1 * | 10/2005 | Dhuper | ............ | A61M 15/0086 128/200.23 |
| 2006/0260606 A1 * | 11/2006 | Coifman | ............ | A61M 15/009 128/200.14 |
| 2007/0283954 A1 * | 12/2007 | Dhuper | ............ | A61M 15/0088 128/203.12 |
| 2008/0035143 A1 * | 2/2008 | Sievers | ............ | A61M 11/008 128/203.12 |
| 2008/0210225 A1 * | 9/2008 | Geiger | ............ | A61M 15/0086 128/200.14 |
| 2011/0132359 A1 | 6/2011 | Poree | | |
| 2013/0192597 A1 * | 8/2013 | McKinnon | ........ | A61M 16/0078 128/203.28 |
| 2013/0276781 A1 * | 10/2013 | Steelman | ........ | A61M 15/0023 128/203.12 |
| 2014/0230817 A1 * | 8/2014 | Richardson | ........ | A61M 15/002 128/203.15 |
| 2016/0256641 A1 * | 9/2016 | Lisberg | ............ | A61M 15/009 |
| 2016/0339187 A1 * | 11/2016 | Smaldone | .......... | A61M 15/0016 |

\* cited by examiner

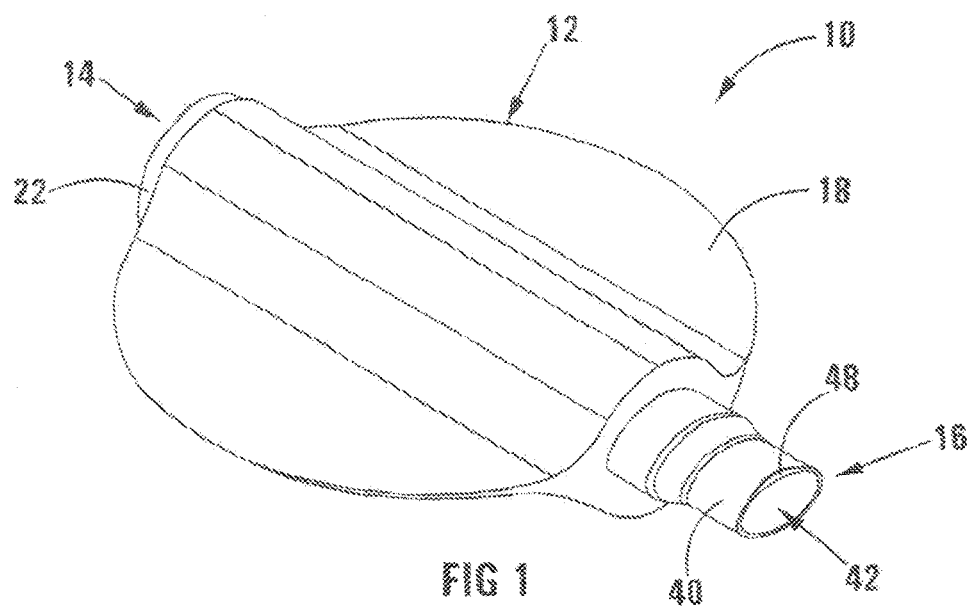
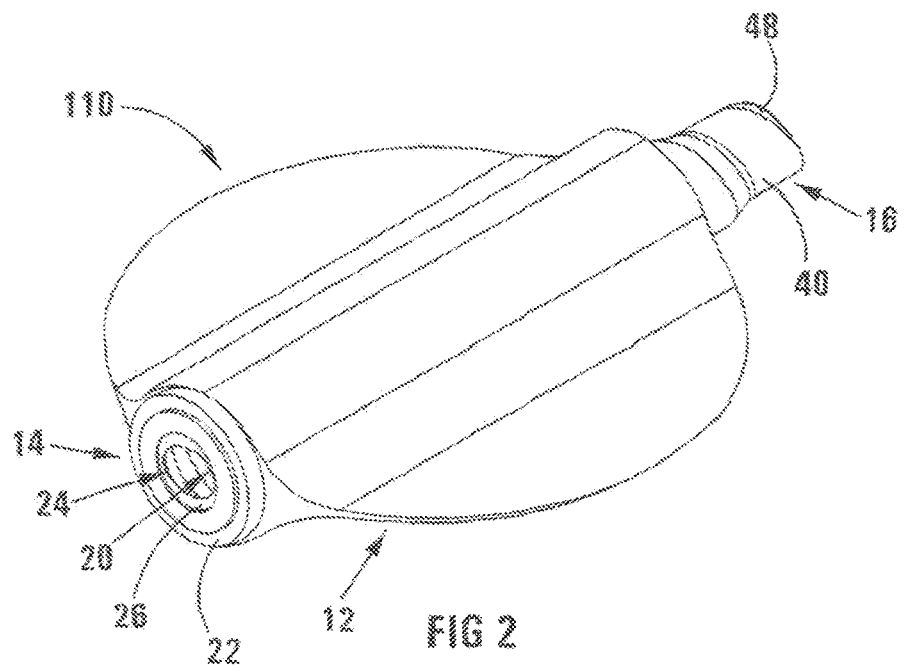

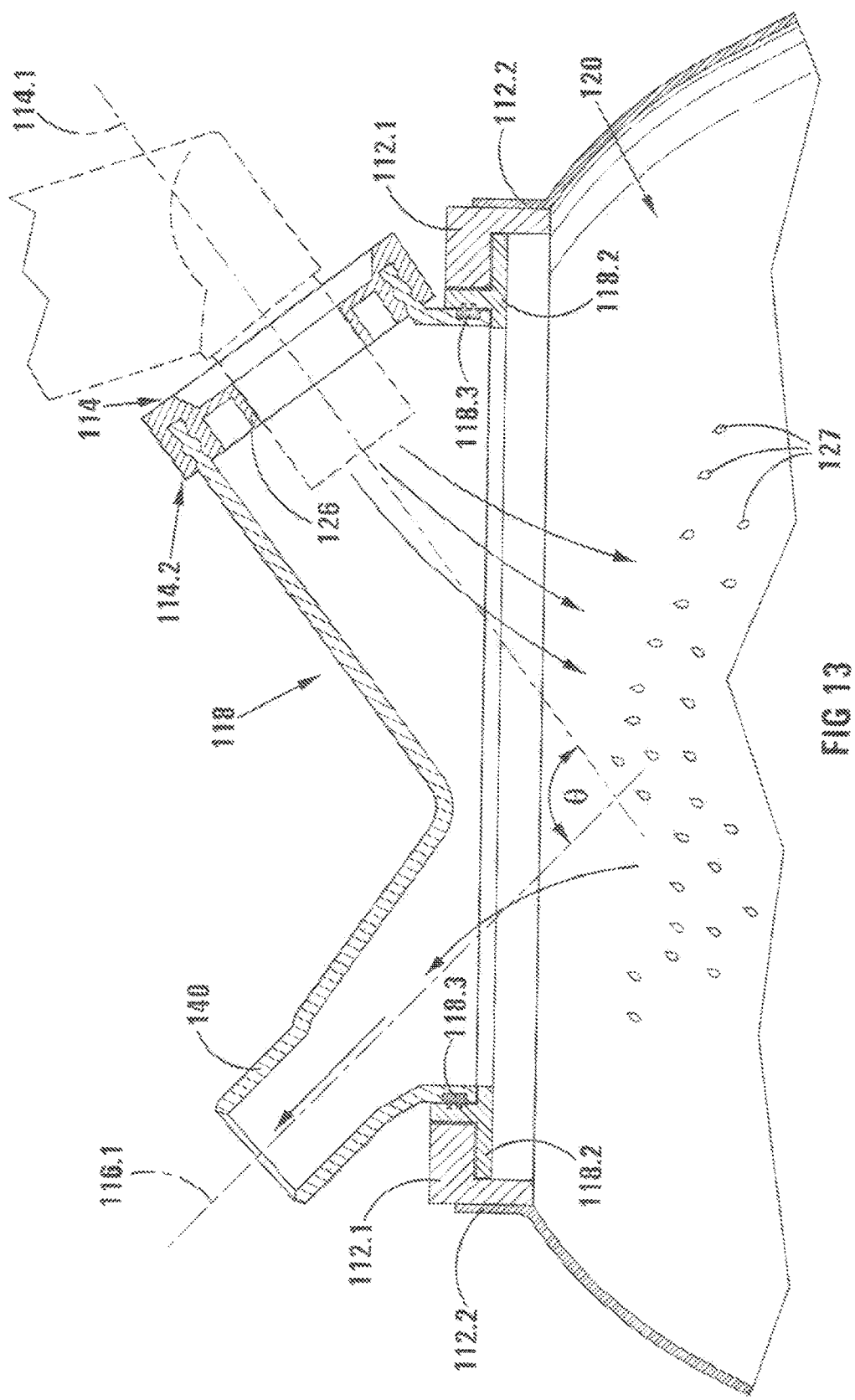

FLEXIBLE BAG SPACER DEVICE FOR AN INHALER

FIELD OF INVENTION

The present invention relates to a spacer device for an inhaler. More particularly, the present invention relates to a spacer device for use during inhalation of medication from an inhalation drug delivery device.

BACKGROUND ART

The following discussion of the background art is intended to facilitate an understanding of the present invention only. The discussion is not an acknowledgement or admission that any of the material referred to is or was part of the common general knowledge as at the priority date of the application. An inhaler or inhalation drug delivery device (IDDD) is a medical device that is used for delivering a medicine or drug to a patient's lungs by oral inhalation. The IDDD is usually in the form of a pressurised aerosol container. A spacer device is a device—usually placed between the IDDD (inhaler) and the patient's mouth (or nose, or both)—which facilitates delivery of medication from the inhaler to the patient. A typical pressurised aerosol container is a metered-dose inhaler (MDI), more commonly referred to as a puffer or as an asthma inhaler, in which the drug is typically provided in solution or suspension within the pressurised container or canister housed in a manual actuator. During use, the mouthpiece of the MDI is placed in the patient's mouth following which the MDI is actuated to express a metered dose of the drug to be breathed in by the patient. Use of such an MDI inhaler could be considered rather intricate as it requires the patient to first fully exhale, then to coordinate inhaling deeply together with actuation of the MDI inhaler, and finally to hold their breath for a period of about ten seconds thereafter to allow the inhaled drug to settle onto the walls of the bronchi and other lung airways. Unfortunately, in this situation, most of the drug emitted from the MDI does not reach the airways intended, and instead, impacts the back of the throat and mouth from where it is swallowed, bypassing the lungs. Even with good timing and technique, the device tends to be extremely inefficient with only about 12% of the dose reaching the appropriate airways. Poor technique reduces this low dose even further, especially in the case of unsophisticated users, the elderly, or children.

Breath-activated inhalers automatically dispense a dose of drug when the patient inhales on the mouthpiece and thereby avoid the need to coordinate inhalation together with the actuation. While this dispenses with the need for coordination, most of the particles still impact the back of the throat and the amount reaching the airways is only minimally increased. Over the past 60 years, inhalation technology has done little to help the average asthmatic or chronic obstructive pulmonary disease (COPD) sufferer—the largest groups of inhalation device users. This is readily demonstrated by the fact that in the vast majority of these patients, the amount of inhaled medication reaching the lungs ranges from less than 10% for those patients using the MDI (metered dose inhaler, or "puffer") straight into their mouth, to between 10 and 30% for those using a spacer device—and this has not improved significantly in all that time. The consequence of this has been huge and expensive drug wastage, poor treatment outcomes, and patient and doctor frustration—all of which has contributed to reduced treatment adherence. In an effort to address these problems, a report published by the European Respiratory Society and the International Society of Aerosolised Medicine (ERS/ISAM) task force in 2011 highlighted three factors that need to be considered in optimising the chances of inhaled medications reaching their targets in the lung. These three factors are:

1. Particle size—smaller particles are more likely to reach the airways in greater numbers, penetrate deeper into the lung, spread more evenly through the lung, pass through partially obstructed airways, and reach diseased and damaged areas.
2. Flow—lower flow rates avoid impaction of particles around corners
3. Breathing pattern—slow, controlled deep inhalation or, if this cannot be achieved, normal relaxed tidal breathing will enhance lung deposition.

Currently there are no inhalation or spacer devices of which the Applicant is aware that cater for all three of these factors collectively, and even when a device attempts to take each factor individually, the performance is not optimal. MDIs when used on their own require a fast, sharp inhalation to capture the short ejection time of the device. This in itself requires supremely coordinated timing of actuation and inhalation, and even when this is achieved (and this occurs rarely), most of the actuated particles will still jettison at high speed on to the back of the throat where they will impact and be retained instead of finding the extremities of the user's lungs. Using currently available spacers of which the Applicant is aware may improve this somewhat although a degree of co-ordination is still required, and a significant percentage (10-40%) of actuated particles may adhere to the walls of the chamber (either by impaction or static electricity, or both). In addition, during exhalation, particles not absorbed are wasted to the atmosphere due to the exit valve closing.

All of these factors become even more pertinent in diseased lungs where most inhaled drugs will preferentially follow the path of least resistance towards the healthier parts of the lung, with very little drug penetrating to areas where it is needed most, such as the peripheral airways, airways clogged with mucus, cavities, and damaged areas. With patients using inhalers without a spacer device, reports quoted in the ISAM report indicate that 76% of patients using a standard MDI and around 50% of patients using a breath-actuated MDI make at least one error when using their inhaler. The most common problems were lack of actuation-inhalation coordination and stopping inhalation due to cold HFA (propellant gas) effect. Use of a spacer device (also known as a Valved Holding Chamber—VHC) can increase the amount of drug reaching the airway from an MDI although with existing spacers, a number of factors limit this increase. Conventional commercial spacer devices of which the Applicant is aware have a breath-activated valve at their mouthpiece to retain the drug within the chamber until inhaled by the patient. The valve closes automatically when the patient exhales and the exhaled air is exhausted to the environment. If the patient inhales incorrectly then a significant percentage of the drug can be lost with the exhalation. Other disadvantages of the valve are that it also creates additional turbulence of inhaled particles affecting flow of medication into the patient's mouth, retains medication impacting on the valve thus reducing amount available for inhalation, and increases resistance to flow thereby influencing the patient's ability to inhale efficiently.

Current spacers of which the Applicant is aware generally come in two sizes—large volume (~800 ml) and small volume (~175-300 ml). Some of these chambers comprise nestable sections that can be collapsed when not in use, but the chamber will, in operation, still be of fixed internal dimension when extended in telescope-fashion during drug delivery. Large volume spacers are bulky and therefore conspicuous by nature causing patients to feel self-conscious when using the device in a social setting. The awkwardness this creates may well contribute to poor technique resulting in reduced efficiency. While the large volume spacer provides a larger reservoir for inhalation, this requires the patient to have the ability to inhale sufficiently deeply, together with an element of timing and co-ordination. If unable, the valve at the mouthpiece—as mentioned earlier—is not an efficient mechanism for re-breathing, and a significant amount of medication will be lost. The small volume spacer is popular with patients as it is considered more socially acceptable, although the small volume itself limits the size of the available reservoir and therefore reduces efficiency of delivery. At the same time, it increases the amount of drug impacting and being retained on the walls of the spacer. Both large and small volume spacers currently all have rigid walls where, again, the likelihood of particles impacting on the wall being retained is increased.

Another known problem with some existing spacer devices is that a static charge can build up inside the chamber that causes particles of the drug to be attracted towards, and adhere to, the interior walls of the chamber. Some existing spacers employ various methods for reducing static electricity with variable results, although none of the current methods completely eradicate it or lower it to levels sufficiently low to have a marked impact on the amount of drug reaching a user's lungs.

Overall, despite the introduction and improvement of IDDDs (as well as patient education), the vast majority of patients using currently available inhalation devices generally receive less than 30% of the actuated dose into their lungs.

It is to be understood that, if any prior art publication is referred to herein, such reference does not constitute an admission that the publication forms a part of the common general knowledge in the art, in Australia, or any other country.

SUMMARY OF THE INVENTION

According to one aspect of the invention, there is provided a spacer device for an MDI, the spacer device comprising:
a body having an inlet and an outlet opposed from the inlet;
a demountable, flexible bag attached to the body, the bag and body together defining a chamber, such that the inlet and outlet are in fluid flow communication with an interior of the chamber;
wherein the inlet is configured to be connected to an MDI containing a drug to be inhaled;
wherein the outlet is configured to be received by a user's mouth; and
wherein the flexible bag serves as reservoir to allow for the formation of a cloud or mist of the drug to be inhaled therewithin following activation of the MDI, the flexible bag being configured to be at least partially inflatable and at least partially deflatable commensurate with breathing and/or rebreathing.

As such, one aspect of the invention provides a valveless spacer device for an MDI, the spacer device comprising:
a body having an inlet and an outlet opposed from the inlet;
a demountable, flexible bag attached to the body, the bag and body together defining a chamber, such that the inlet and outlet are in fluid flow communication with an interior of the chamber;
wherein the inlet is configured to be connected to an MDI containing a drug to be inhaled;
wherein the outlet is configured to be received by a user's mouth; and
wherein the flexible bag, following actuation of the MDI, serves as a reservoir allowing for the formation of a cloud or mist of the drug therewithin which is then ready for inhalation, the flexible bag being configured to be at least partially deflatable and at least partially inflatable commensurate with a single breath and/or rebreathing.

The body, including the inlet and outlet, may be configured to reduce a static electricity charge. The bag may be configured to reduce a static electricity charge. The body (including inlet and outlet), and/or bag may be treated with an antistatic agent. The body (including inlet and outlet), and/or bag may be made of electrically conductive material. The body, including the inlet and/or outlet, may be made of metal or a metallised compound, such as metallised plastic or a metal-coated plastic. The bag may be made of a metallised film or aluminium foil. The metallised film may be a metallised polymer film.

The inlet may comprise a mount defining an inlet passage for sealingly engaging with a mouthpiece of an inhalation drug delivery device. The inlet may be configured to sealingly receive a mouthpiece of an MDI inhaler. The inlet may be surrounded by a sealing collar configured to seal against the inhalation drug delivery device. The spacer device, including the inlet and outlet, may be valveless. The outlet may comprise a mouthpiece defining an outlet passage. The outlet passage may provide unimpeded air and drug flow between the chamber and the ambient environment or, during use, the person's mouth.

In one, preferred, embodiment of the invention, the body is external to the bag. The bag may depend operatively downwardly from the body. In this embodiment, the body is in the form of a generally V-shaped mounting. The V-shaped mounting may be formed by the opposing inlet passage and the outlet passage intersecting at an angle along their respective longitudinal axes where the angle creating the V defines an arc of preferably between 30 and 170 degrees, preferably 60 to 120 degrees, most preferably 90 degrees. The inlet and outlet passages may be cone-shaped. The perimeter of the inlet may be round, oval, elliptical, or irregular in shape. The V-shaped mounting may include a V-shaped interior surface, and may have a lower perimeter formed by the merging of the inferior and lateral aspects of the merging inlet and outlet ports that is generally oval in shape. This perimeter may constitute the portion of the mounting that receives the demountable bag. The interior of the V-shaped mounting is shaped and dimensioned to define a cavity that provides a passage for flow of air and/or medication between the inlet and the bag and between the bag and the mouthpiece. The interior of the V-shaped cavity may be sized and dimensioned to receive the bag, when the bag is folded into the cavity for portability purposes.

The inlet and outlet passages may be of roughly equal proportion in size, length, volume, diameter, or shape. The inlet and outlet may, in another embodiment, not be proportional in size, length, volume, diameter and/or shape.

The ratio of the major and minor axes of the oval perimeter in this embodiment may be between 1.01:1 and 6:1, preferably between 1.2:1 and 2:1, most preferably 1.38.

The outlet may be configured to be received by a user's mouth, either directly, or through a face mask.

The invention extends in a further aspect thereof to a bag for a spacer device of the invention, wherein the bag has an opening including a collar that is shaped and dimensioned to fit securely to the lower perimeter of the body of the spacer device of the invention, thereby to releasably attach the bag to the body of the spacer device. The collar may extend along an upper periphery of the bag opening, and may extend at least partially around the opening of the bag. The bag opening may be biased towards an open, distended position by way of being made of a resiliently flexible material. The bag when ready for use, may spontaneously adopt a shape of an open inflated/distended position. This may occur through shape or material memory. The bag may be provided with a peripherally extending, resiliently flexible seam. The resiliently flexible seam serves to resist vertical collapse of the bag during inhalation and exhalation.

The capacity for the bag to adopt this shape may be engineered to ensure that negligible resistance to the collapse of the bag during inhalation is present. The collar may be made of a resiliently flexible material that urges the collar (and hence bag) against an inner surface of the mounting, in one embodiment. In another embodiment, the collar may be shaped and dimensioned to encircle and attach in a friction-fit—including an O-ring conformation—or snap-fit manner to the lower perimeter of the body. The bag may also be provided with a threaded collar that engages with a complementarily threaded portion of the lower perimeter of the body.

It is to be understood that the spacer device may include bags of many different sizes and shapes, with the choice depending on a number of factors including, but not limited to: the lung volume and inhalation capabilities of the user; the medical needs at the time of use; and the patient preference (which may include merchandising choices) or to minimize awkwardness and conspicuousness when used in social settings.

In one embodiment of the invention, the body may be internal to the bag. In this embodiment, the body may comprise a frame joining the inlet to the outlet. In this embodiment, the frame may be configured to define a tunnel between the inlet and the outlet and to prevent occlusion of the tunnel when the bag is deflated. In this embodiment, the frame may comprise struts or braces being configured to prevent the bag from collapsing completely in use during deflation thereof, thereby to prevent the tunnel being closed or becoming blocked.

BRIEF DESCRIPTION OF DRAWINGS

The present invention will now be described, by way of example, with reference to the accompanying schematic drawings, in which:

FIG. 1 is a front perspective view of a spacer device for an inhaler according to an earlier embodiment of the invention having a bag supported on a frame (body);

FIG. 2 is a rear perspective view of the spacer device shown in FIG. 1;

FIG. 13 is a cross-sectional view of the embodiment shown in FIGS. 10 to 12B, showing the flow of droplets expelled from the MDI leading to the formation of a cloud or mist traversing the cavity defined between the body and the bag;

DETAILED DESCRIPTION OF THE INVENTION

Figure 3:
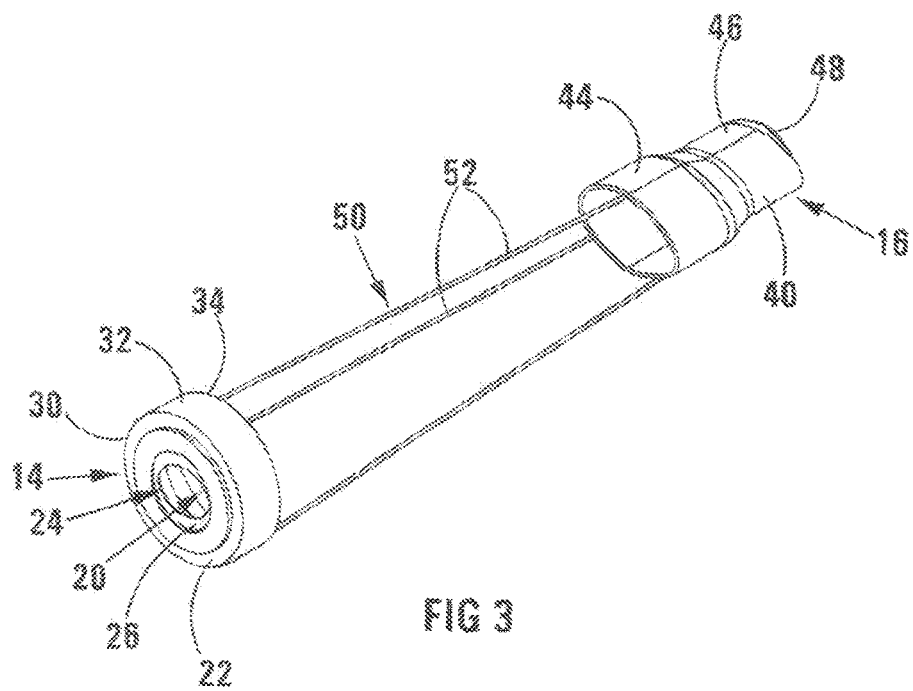
FIG. 3 is rear perspective view of the frame (body) of the spacer device.

The invention as described herein relates to a spacer device for facilitating inhalation of medication delivered from an inhaler delivery device (such as an MDI).

Initially, the first embodiment of the invention, shown in FIGS. 1 to 9 was developed, and this was further refined into the preferred embodiment of the invention shown in FIGS. 10 to 19.

In general, the spacer device of the invention includes a flexible, collapsible bag shaped and dimensioned to serve as reservoir for receiving a drug to be inhaled in a mist or cloud form, and a body (also referred to herein as a "base") with an inlet, or entrance, through which medication is discharged from an MDI into the bag, and an outlet, or exit, forming a mouthpiece through which the contents of the bag can be inhaled with the bag collapsing under the negative pressure created by the inhalation thereby promoting the emptying of all its contents into the mouth of the patient and maximising the delivery of medication to the lungs of even unsophisticated users. The spacer device allows for a full dose of inhalant drug to be received within the bag, from where it can be inhaled slowly (and completely) by an unsophisticated user by way of regular, tidal breathing. The elements of the spacer device are designed to minimize impaction of drug particles therein or thereupon, thereby promoting laminar flow into and out of the bag and ports. This arrangement greatly facilitates increased drug availability and inhalation, allowing the inhalant drug to progress into the furthest stretches of the user's lungs with having to coordinate the emission of the inhalant drug into the bag with inspiration. Increased levels of drug can be inhaled by regular, tidal breathing rather than the sharp, co-ordinated inspiration that is required with other inhalation devices and spacers of which the Applicant is aware. Usefully, the size of the bag can be swapped to suit a user's needs—age, physical size, lung capacity, strength of inspiration, social awkwardness—and it has been found that a bag as small as 500 $cm^3$ and as large as 1500 $cm^3$ can achieve similar levels of drug particles being inhaled successfully, depending on the factors named above.

Referring to the drawings, reference numeral 10 refers generally to a spacer device according to one, earlier, embodiment of the invention, shown in FIGS. 1 to 9, while reference numeral 110 refers generally to a spacer device according to a second (preferred) later embodiment of the invention.

FIGS. 1 to 9 illustrate an earlier embodiment of the invention wherein the bag encloses the body (in this embodiment, the body is in the form of a framework), while the remaining Figures show a further embodiment of the invention wherein the bag is attached to, but external to the body.

In FIG. 1, there is shown a spacer device 10 in accordance with one embodiment of the invention for use with an inhalant drug delivery device (IDDD) for inhalation. The IDDD can be an MDI inhaler, a dry powder inhaler, or any other inhaler for use with aerosolised drugs, dry powder drugs or other drug formats). In this embodiment, the spacer device 10 comprises an inflatable bag 12 having an inlet 14 being provided at one end of the bag and an outlet 16 being provided at an opposed end of the bag 12.

Figure 5:
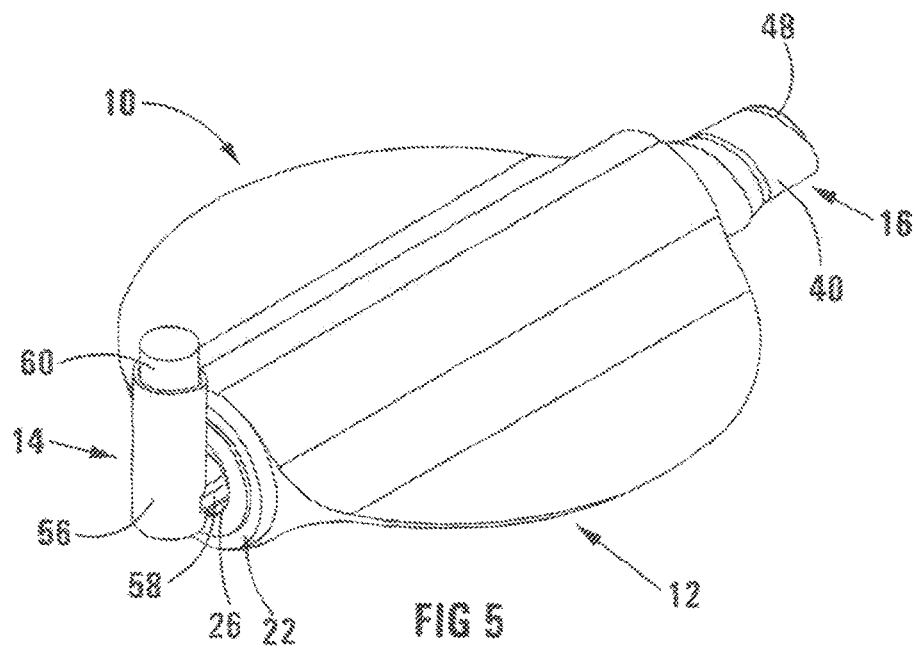
FIG. 5 is a rear perspective view of the spacer device shown ready for use with an inhaler attached thereto and with the bag deflated.
Figure 6:
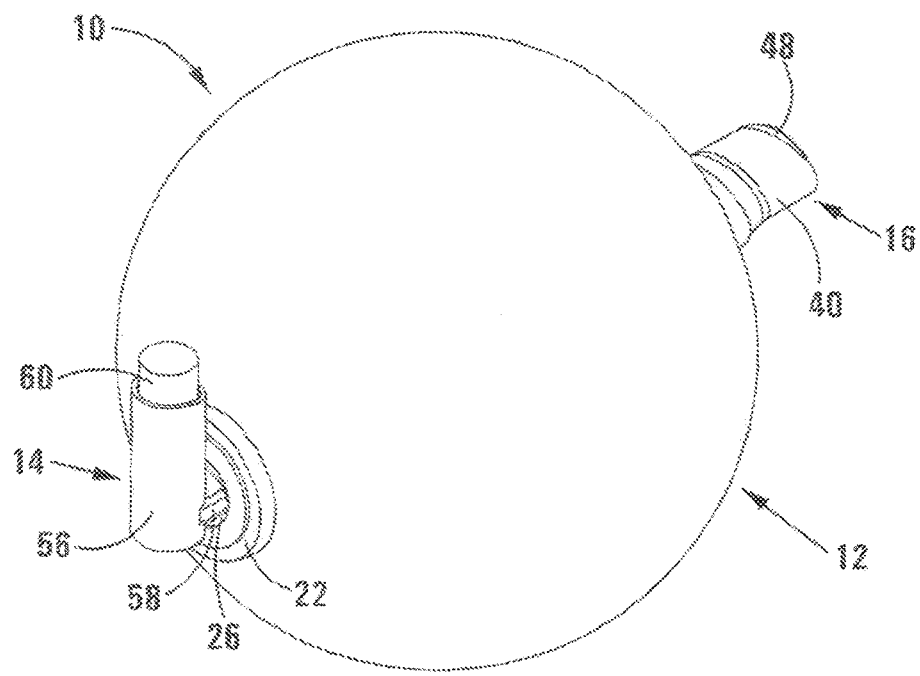
FIG. 6 is a rear perspective view of the spacer device with inhaler of FIG. 5, but with the bag inflated.

The bag 12 is in the form of a balloon that is roughly disc-shaped when deflated (see FIGS. 1 and 2) and roughly spherical when inflated (see FIGS. 5 and 6). However, the bag 12 can have other shapes as desired, for example such as being ovoid, elliptical, lenticular, frusto-conical, or rugby-ball shaped when inflated. The bag 12 can be constructed with one or more seams 12.1 made of, or containing, a resiliently flexible or shape-memory material providing the bag with shape memory that opens the bag 12 in the inflated position when preparing it for use. The one or more seams 12.1 may also control the way the bag 12 deflates in a predetermined manner if necessary to enhance both the functioning thereof during deflation as well as to improve its aesthetics. The bag 12 can be non-symmetrical so that, for example, it has a larger inflated volume on an operative lower side thereof or vice versa. In another embodiment (not shown), the bag includes include concertina-like folds for the same purpose.

In FIGS. 1 to 9, the bag 12 is in the form of a flexible, non-distensible bladder that, together with, inlet 14, and outlet 16 define a body 18, the bag 12 and body 18 forming a chamber 20. In one embodiment the bag 12 is made of an electrically conductive material, such as a metal or aluminium foil. In another embodiment the bag 12 is made of a metallised film or metallised biaxially-oriented polyethylene terephthalate (BoPET) or other similar flexible polymer, typically Mylar®. Alternatively, the bag 12 can be treated with an antistatic agent forming a static dissipative coating or layer on the bag 12. The same applies to the body 18, which can be made from, laminated to, or coated with, an anti-static coating or layer, such as a metal.

The chamber 20 has a volume sufficiently large that the bag 12 cannot be overinflated or fully deflated (collapsed) in normal use during breathing by a person. In this regard, the volume of the bag 12 can be selected dependent on the age of the person such that a smaller bag 12 is provided for a younger person, while a larger bag 12 is provided for a larger person.

The inlet 14 is in the form of a socket configured to receive an outlet from an inhalant drug-delivery device (IDDD), such as a mouthpiece of an MDI inhaler (best shown in FIG. 5, reference numeral 58). The inlet 14 includes a mount 22 defining an inlet passage 24 into the chamber 20. A sealing collar 26 is attached to the mount 22 to surround the inlet passage 24. The collar 26 is contoured so that the inlet passage 24 is substantially complementary to the shape of the IDDD mouthpiece. The collar 26 is also resiliently flexible so that it can cater for minor variations in the shape of the mouthpiece and conform in sealing contact therewith. When the IDDD mouthpiece is attached to the inlet 14, the IDDD mouthpiece is pressed into the inlet passage 24 by press-fit so that the collar 26 annularly seals against the IDDD mouthpiece.

In this embodiment the mount 22 comprises a substantially circular disc 30 with an annular skirt 32 depending from the disc 30 and leading to edge 34. The inlet passage 24 is circular in shape, although it may be shaped in other embodiments to be conformable to a wide range of IDDD mouthpieces and may also be sold in kit form.

The collar 26 is roughly Y-shaped in appearance in cross section having opposed flanges 36 (the two "arms" of the "Y") defining an annular outer groove 38. The collar 26 is joined to the mount 22 by locating the disc 30 in the groove 38 so that the disc 30 is held between the opposed flanges 36. The "foot" of the "Y" defines the inlet passage 24.

In other embodiments, the inlet passage 24 can be shaped to be substantially complimentary with the IDDD mouthpiece with the collar 26 having a regular cross-section. For example, such a collar 26 could be shaped as a flexible torus with an outer groove so that it could be clipped over the edge of the disc 30 surrounding the inlet passage 24. Alternatively, the disc 30 can be made thicker and the collar 26 could be an O-ring held within a groove provided in the disc 30 within the inlet passage 24.

The mount 22 can optionally include a connector (not shown) arranged to be inserted into the inlet 14 to accommodate different types of IDDDs. The mount 22, and connector if provided, is made of an electrically conductive material to avoid build-up of static electricity or, alternatively, is coated with an antistatic agent.

The outlet 16 comprises a mouthpiece 40 defining an outlet passage 42. The mouthpiece 40 is substantially rigid so that it cannot be deformed or pressed closed. The mouthpiece 40 is ovoid, circular, lenticular, or elliptically shaped in its cross-section being transverse to the operative direction of the outlet passage 42, thereby being generally complementary in shape with a person's mouth so that is can be sealingly received in their mouth. However, it should be appreciated that the mouthpiece 40 can have other shapes that are suitable for being received in a patient's mouth, e.g.

circular cylindrical. Thus the outlet passage 42 is normally open so that the chamber 20 is in free communication with the ambient environment when the mouthpiece 40 is not sealingly held in a person's mouth.

The mouthpiece 40 has a proximal end 44 and a distal end 46. The mouthpiece 40 is flared towards its proximal end 44 such that the outlet passage 42 is wider at its opening into the chamber 20 and narrower at the distal end 46 leading to the environment or the person's mouth in use. Thus in use the mouthpiece 40 is shaped to funnel the airflow and drug from the chamber 20 into the patient's mouth. In one embodiment the mouthpiece 40 has an outwardly projecting ridge 48 partially or fully surrounding the outlet passage 42 at or near its distal end 46. The ridge 44 is configured to be trapped by the person's lips to limit or prevent slippage of the mouthpiece 40 through their lips during use. In other embodiments, no ridge is provided and the person merely uses lip pressure to prevent slippage.

The mouthpiece 40 is made of an electrically conductive material to avoid build-up of static electricity or, alternatively, is coated with an antistatic agent.

The bag 12 is joined to the mount 22 by attachment to the skirt 32. Similarly, the bag 12 is joined to the mouthpiece 40 by attachment to the proximal end 44 of the mouthpiece 40. In one embodiment the bag 12 is permanently attached to the mount 22 and the mouthpiece 40; such permanent attachment could be formed by adhesive or by welding using heat or ultrasound. In another embodiment the bag 12 is replaceably or demountably attached to the mount 22 and the mouthpiece 40; such releasable or demountable attachment could be formed by adhesive or by mechanical constriction such as by using elastic bands wrapped around a part of the bag 12 extending over the mount 22 and the mouthpiece 40. The bag 12 can have an integrally formed resilient rib, such as is typically found at an opening of a conventional party balloon, being configured to be clipped onto the mount 22 and the mouthpiece 40. The rib may be elastic or, in this embodiment, be biased to be resiliently constrictive or cinched to grip the mouthpiece 40. The rib is, in certain embodiments, provided with an elasticated purse-string arrangement.

As can be more clearly seen in FIG. 3, the body 18 of the spacer device 10 includes a frame 50 extending between the mount 22 and the mouthpiece 40. The frame 50 comprises three rods 52 extending from the edge 34 of the skirt 32 to the proximal end 44 of the mouthpiece 40. In other embodiments, the frame 50 can comprise four or more rods 52. The rods 52 are substantially equidistantly spaced from each other along the perimeter of the edge 34. The frame 50 is configured to perform two functions during use. Firstly, the frame 50 provides rigidity to the spacer device 10 so that the mount 22 and mouthpiece 40 are held joined but spaced apart from each other. This assists a person in holding the spacer device 10 with one hand while using their other hand to actuate the IDDD inhaler. Secondly, the frame 50 forms a strut preventing the bag 12 from completely flattening when deflated, i.e. so that a tunnel remains open between the mount 22 and the mouthpiece 40. In this regard, the frame 50 can comprise cross-braces extending between the rods 52 to prevent the bag 12 from being sucked in between the rods 52 during deep inhalation. The frame 50 can also comprise rings encircling the rods 52.

Figure 8:
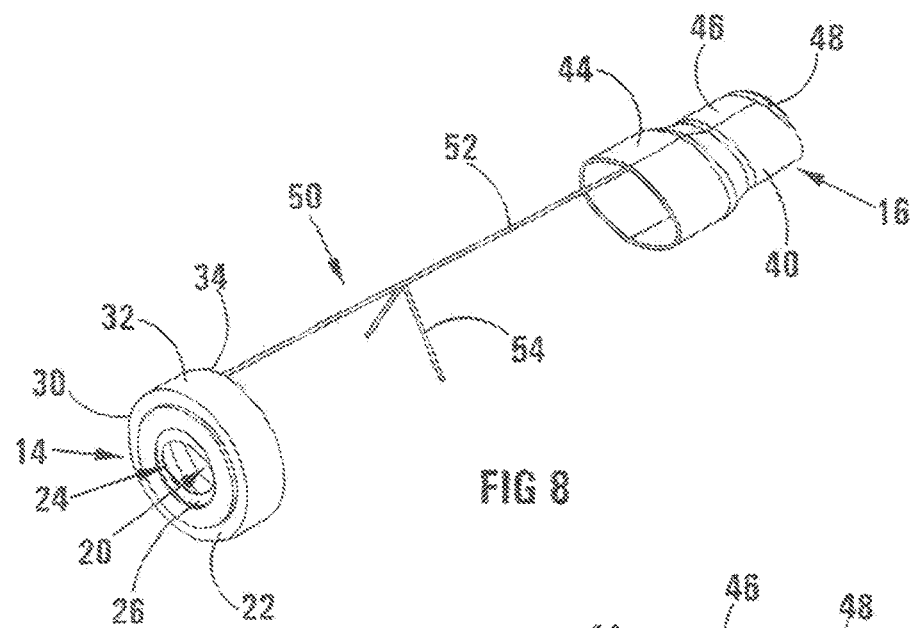
FIG. 8 is a rear perspective view of a second embodiment of the frame of the spacer device.

A second embodiment of the spacer device 10 is shown in FIG. 8, in which the frame 50 comprises a single rod 52 that has prongs 54 projecting outwardly therefrom and being configured to prevent flattening of the bag 12 when deflated. The prongs 54 can be provided in pairs extending outwardly from the rod 52. More than one pair of prongs 54 can be provided along the length of the rod 52. The prongs 54 can extend perpendicularly from the rod 52 or they can be inclined longitudinally relative to the rod 52.

The frame 50 is made of an electrically conductive material, such as metal. In another embodiment the frame 50 is coated with an antistatic agent forming a static dissipative coating or layer.

Figure 4:
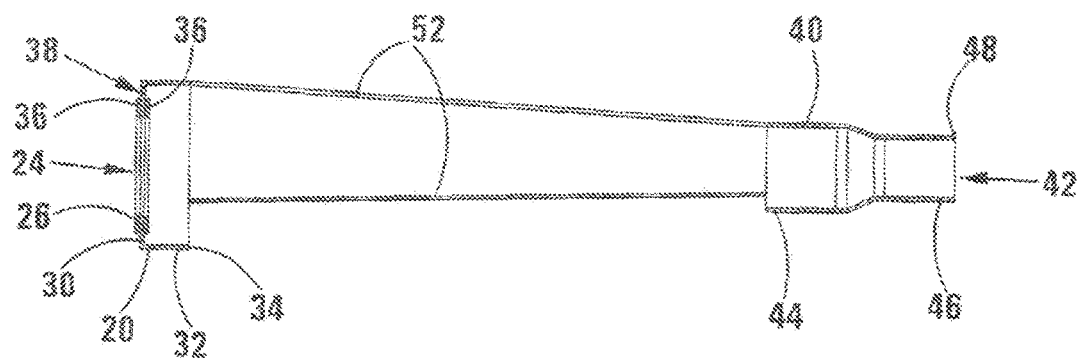
FIG. 4 is a sectional side view of the frame (body) FIG. 3.

Referring now also to FIGS. 4 to 6, in use with a conventional IDDD such as an MDI, a person will initially attach their IDDD inhaler 56 to the spacer device 10 by inserting the IDDD mouthpiece 58 into the inlet passage 24 so that the collar 26 seals around the IDDD mouthpiece 58. The person then places their mouth over the mouthpiece 40 and exhales into the bag 12 to at least partially inflate the bag 12. At this stage the person actuates the IDDD inhaler 56 by pressing on the IDDD canister 60 in conventional manner so that a dosage of drug is dispensed from the IDDD canister 60 into the chamber 20. Thereafter the person breathes in a normal manner (sometimes referred to as tidal breathing) to inhale the drug from the chamber 20 and exhale into the chamber 20 and during such re-breathing the bag 12 will inflate and deflate as shown in FIGS. 4 and 5. It is expected that such re-breathing will effectively clear the drug dosage from the bag 12 within three to five inhalations by the person.

Such normal tidal breathing is performed at low flow rates and thus the drug is not sucked towards and impacted at the back of the mouth causing it to be deposited in the pharyngeal region. More of the drug is thus breathed into and distributed in the lungs effectively. Due to the regular and normal manner of breathing it is not expected that the person will inhale sufficiently to fully deflate the bag 12 or to exhale sufficiently to fully inflate the bag 12. Nevertheless, should a deep inhalation be taken, the bag 12 will not fully collapse in any event due to the frame 50 maintaining the tunnel open between the mount 22 and the mouthpiece 40. Furthermore, should the bag 12 be substantially deflated, and the user continues to inhale, sufficient negative pressure may be generated to allow ambient air to be entrained through the attached MDI 56 and to flow through the tunnel and in the process help to flush any residual medication in the bag into the lungs.

The fully open outlet passage 42 does not impede breathing by the person at all during use. Any drug that has been inhaled but that has not deposited on the lung walls, is exhaled back into the bag 12 and then subsequently re-enters the lungs when the person inhales again. Thus the drug is not exhausted to the environment as occurs with some prior art spacer devices.

Figure 9:
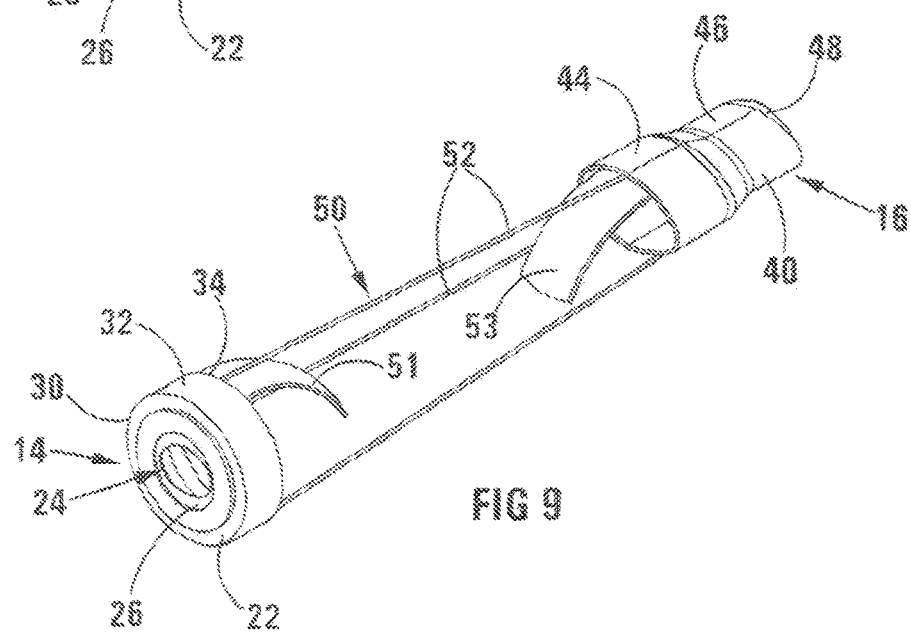
FIG. 9 is a rear perspective view of the frame of the spacer device shown provided with deflectors.
Figure 10:
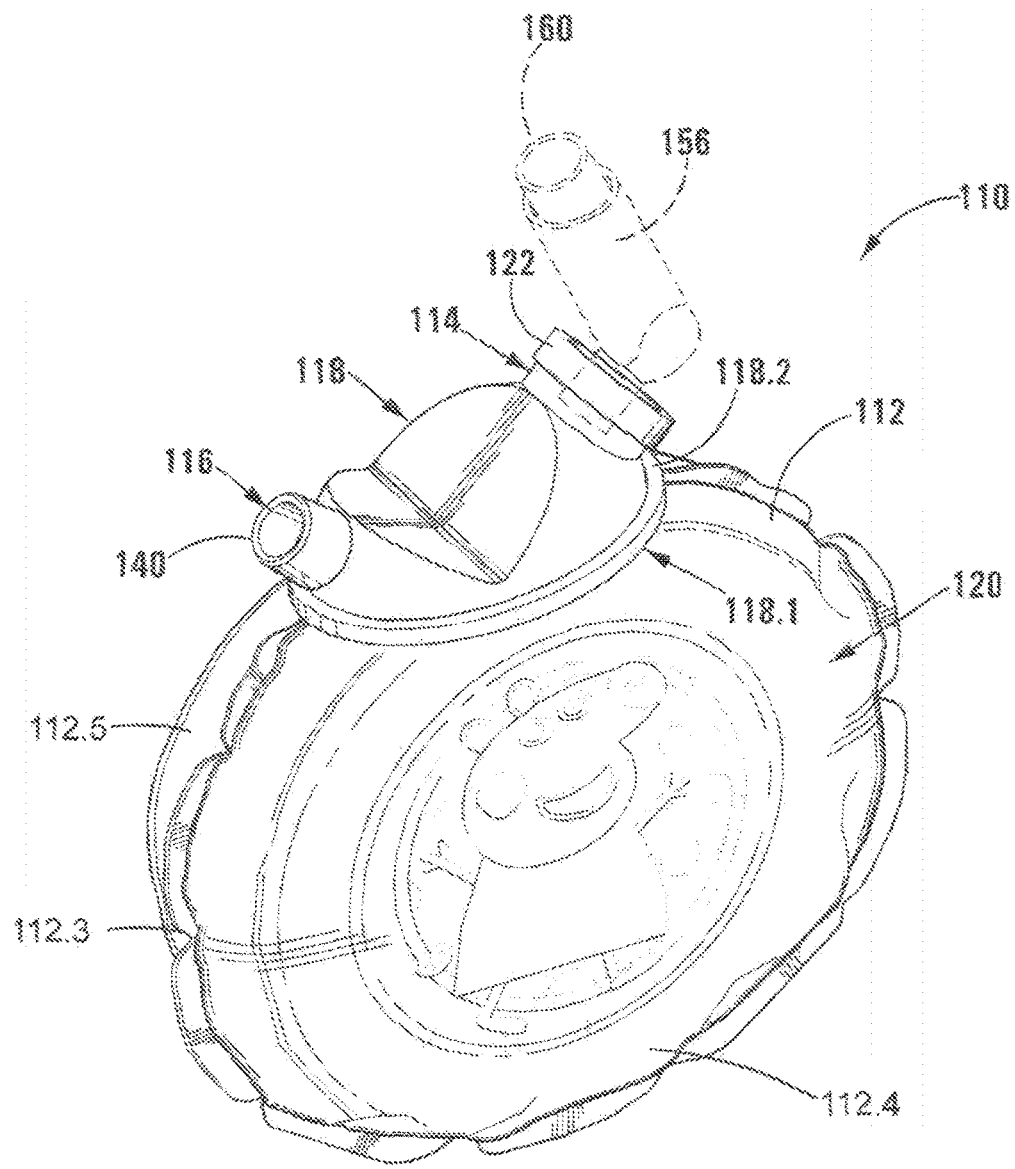
FIG. 10 is a 3-D view of a spacer device in accordance with another, later embodiment or the invention wherein the body is in the form of a V-shaped solid mounting, and wherein the body is external to the bag.
Figure 11:
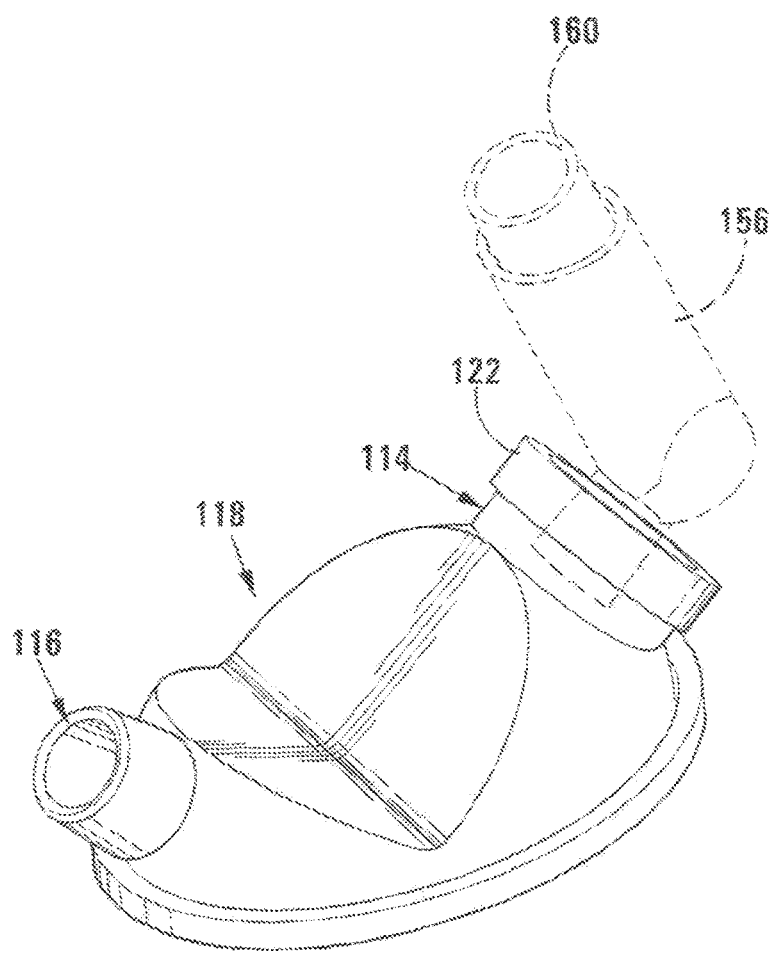
FIG. 11 is a 3-D view of a mounting of the embodiment shown in FIG. 10.

In non-symmetrical bags 12 that have a larger volume on one side of the frame 50, for example so as to hang below the frame 50, the frame 50 can include one or more deflectors 51, 53 (as can be seen in FIG. 9). The deflectors 51, 53 are curved to direct a relatively smooth flow of air and drug movement during use. As such the deflector 51 directs air and drug flow from the inlet passage 24 into the chamber 20. During subsequent patient inhalation, the deflector 53 directs air and drug flow from the chamber 20 through the outlet passage 42 and thereafter, during patient exhalation, the deflector 53 directs airflow, together with any residual drug if present, from the outlet passage 42 back into the chamber 20 for subsequent re-inhalation.

The antistatic nature of the spacer device 10 avoids static electricity in the body 18 from attracting drug particles and preventing the drug particles from being inhaled.

A further benefit of having a flexible bag 12 is that the person can see the bag inflate and deflate during use and this provides the user—as well as the observer (parent or doctor)—with important visual feedback confirming that the drug is being inhaled. The bag 12 can optionally also include a moveable and/or inflatable figurine on an upper side thereof that is configured to stand erect when the bag 12 is inflated and that collapses when the bag 12 is deflated. The figurine is particularly directed to providing incentive and positive feedback to children while using the spacer device 10 to both entertain them and confirm that they are breathing correctly.

In another embodiment of the invention (which is the preferred embodiment resulting from tests done on the first embodiment and is shown in FIGS. 10 to 19), the spacer device 110 comprises a metallised, anti-static or low-static bag 112 of low, or no, distensability attached to a body 118. The bag 12 is made of an electrically conductive material, such as a metal or aluminium foil. In another embodiment, the bag 12 is made of a metallised film or metallised biaxially-oriented polyethylene terephthalate (BoPET) or other similar flexible polymer, typically Mylar®. Alternatively, the bag 112 can be treated with an antistatic agent forming a static dissipative coating or layer on the bag 112. The same applies to the body 118, which can be made from, laminated to, or coated with, an anti-static coating or layer. The body 118 is typically made from a metal such as aluminium (although not restricted to this) or a metallised compound (such as metallised plastic, although not restricted to this), or a metal-coated compound such as a high-density plastics material (although not restricted to this).

The body 118 includes inlet 114 and opposed outlet 116, the inlet 114 and opposed outlet 116 being provided on, and integral with, the body 118. The body 118 and bag 112 combine to form chamber 120 for receiving aerosolised medication.

The inlet 114 and outlet 116 each are in the form of a port that is in fluid flow communication with the chamber 120. The inlet 114 and outlet 116 define, and are separated by, a broad V-formation formed as part of the body 118. The body 118 further includes an elliptical or oval lower perimeter 118.1 defining flange 118.2, for demountably receiving bag 112.

Figure 19:
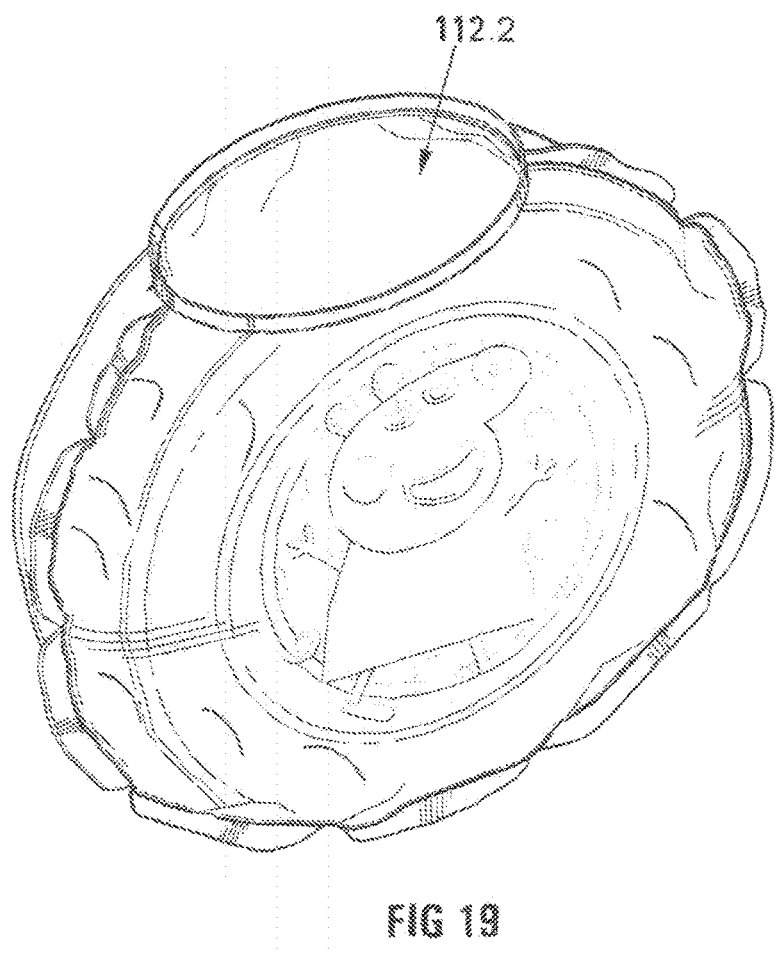
FIG. 19 is a 3-D view of a bag with a collar for attaching to a lower perimeter of the body in accordance with one aspect of the invention, for use with the spacer device shown in FIGS. 10 to 18.
Figure 20:
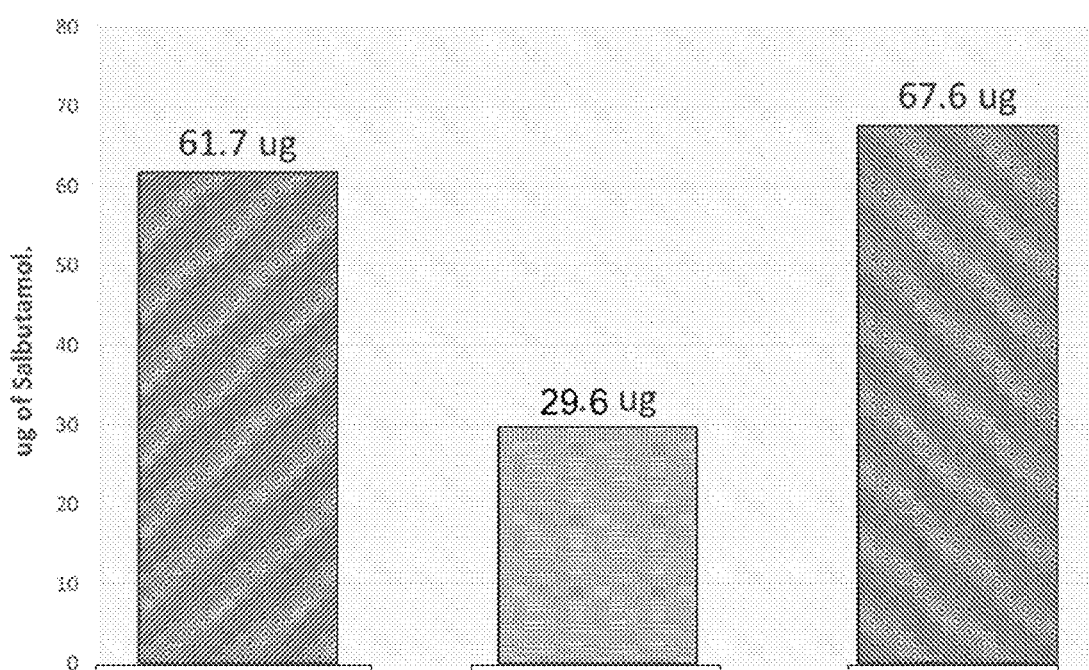
FIG. 20 shows the results of testing of the spacer devices in accordance with the invention.

As may best be seen in FIG. 13, the bag 112 includes a connecting formation in the form of an elasticated, peripherally co-extensive rib 112.1 attached to an opening 112.2 (best seen in FIG. 19) defined within an operatively upper section of the bag 112. The rib 112.1 attaches to the flange 118.2 to provide an effective seal between the bag 112 and the body 118. FIG. 19 also provides an indication of how the bag 112 looks prior to being connected to the perimeter of the base.

In another embodiment (not illustrated), the bag 112 opening 112.2 (and hence rib 112.1) is received over—and thus covers—the flange 118.2, the bag 112 having a constrictive elastic rib or O-ring 112.1 that can provide an effective seal between the bag 112 and the flange 118.2.

The embodiment shown in FIG. 13 shows that the flange 118.2 can be threadedly mounted to the body 118 using thread formations 118.3 to facilitate cleaning or autoclaving of the body 118. In other embodiments shown in FIGS. 11, 14, and 17, the flange 118.2 is formed integrally with the body 118.

Returning to FIG. 10, the inlet 114 includes an annular connector 122 for receiving a mouthpiece 158 of an MDI 156 in fluid flow fashion to the inlet 114, thereby allowing direct communication between the MDI 156 and the chamber 120 to allow for generally unimpeded cloud formation within the chamber 120 when a propellant contained within pressurised canister 160 is released. The annular connector 122 is screwed or clipped on to an end 114.2 of the inlet 114 using threads or interference fittings 114.3 provided proximal said end 114.2. It is to be understood that the annular connector 122 can also be connected to the inlet 114 in a snap fit or friction fit manner (not shown). The annular connector 122 includes a sealing collar 126 in the form of a resiliently flexible inner annulus for sealingly receiving the mouthpiece 158. The annular connector 122 is similar in fashion to connector 22, shown in the embodiment shown in FIGS. 1 to 9.

Figure 14:
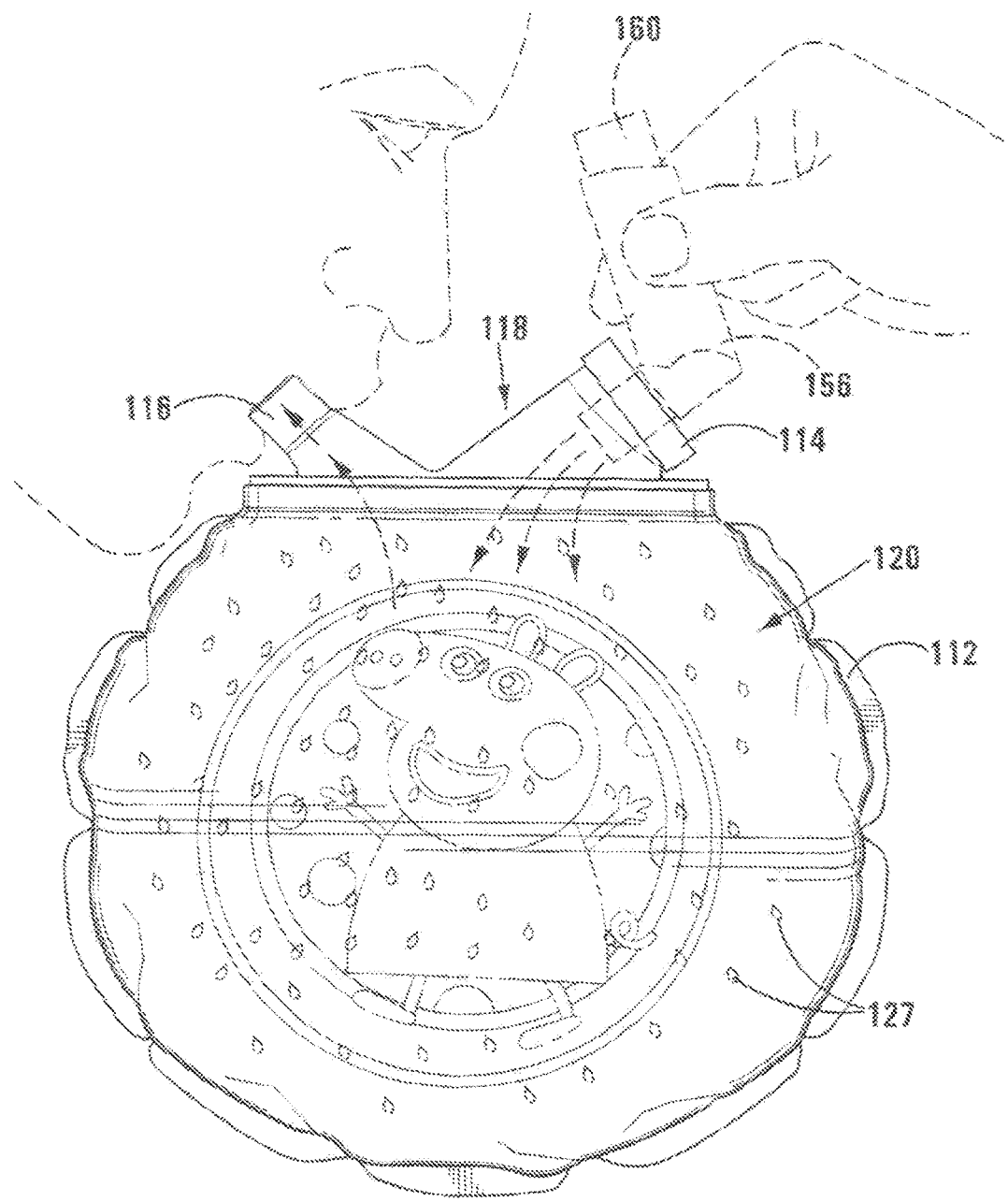
FIG. 14 is a further cross-sectional view of the embodiment of the invention shown in FIGS. 10 to 13, when in use showing the cloud or mist now filling the volume of the bag, ready for inhalation.

As may best be seen in FIG. 13, and as mentioned hereinbefore, the body 118 has the inlet 114 and outlet 116 ports integrally formed therein, in unitary construction, such that the longitudinal axes 114.1, 116.1 of the inlet and outlet ports, respectively, when intersected, define an arc having an angle (shown as Θ) of between 30 degrees and 170 degrees. The V-shape defined by the inlet 114 and outlet 116 ports has a general angle of 90 degrees which corresponds generally to angle (Θ) which is similarly approximately 90 degrees in the embodiment shown in FIGS. 11 to 19. As shown in FIG. 14, this assists in ensuring that the inhalant drug (shown as microdispersion droplets 127) is guided into and fully enters the chamber 20 first rather than being passed directly through between inlet 114 and outlet 116 as would have been the case if they had been in register, i.e. when the angle (Θ) would have been 180 degrees or thereabouts.

In this way, the inhalant droplets 127 enter the chamber 120 in a smooth fluid flow manner without impacting and thereby depositing either on internal structures to any great extent, nor being expelled at speed directly into the oral cavity or throat of the user by shooting directly through outlet 116. The chamber 120 thus serves as reservoir for the inhalant drug and facilitates vapour or cloud formation within the chamber 120, from where the inhalant droplets 127 can be inhaled at a tempo and velocity that the user is comfortable with, without significant loss of drug to the atmosphere or external environment—both during inhalation and/or subsequent exhalation. The angle of the inlet 114 and outlet 116, combined with the smooth, unimpeded entry of the inhalant droplets 127 into the chamber 120, allow for a much higher percentage of the active drug to be inhaled by a user through outlet 116 than would have been the case without such an arrangement, as may best be seen in FIG. 14.

Furthermore, the provision of the bag 112 on the operative underside of (i.e. depending downwardly from) the body 118 ensures that the bag 112 does not impede visual referencing of the inhaler device 156 by the user during use (see FIG. 14), leading also to more accurate, yet less conspicuous, use of the device 110 by the user.

Figure 12A:
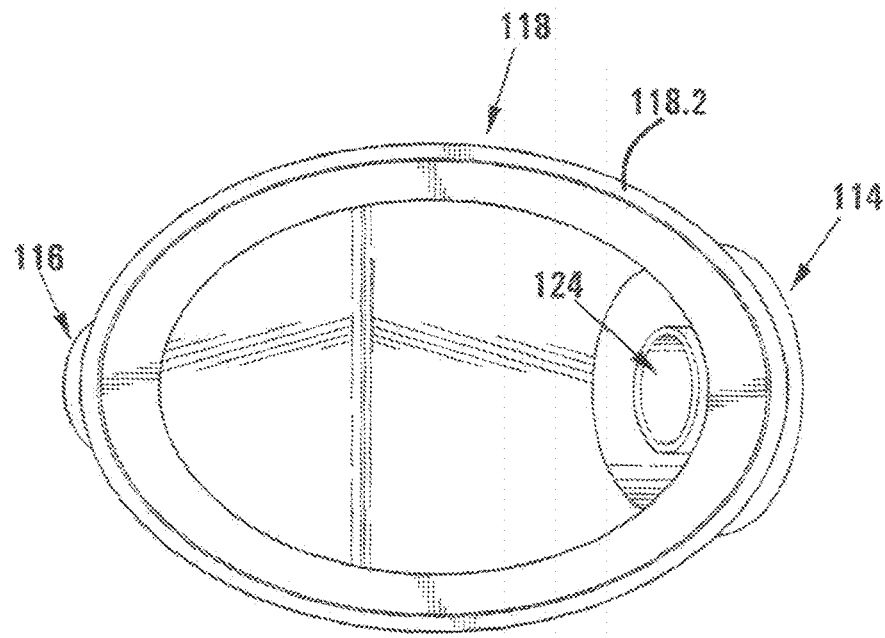
FIG. 12A shows a bottom plan view of a body of the spacer device of the invention wherein the extent of protrusion of the mouthpiece of the inhaler is visible (but the body of the inhaler is not shown)
Figure 12B:
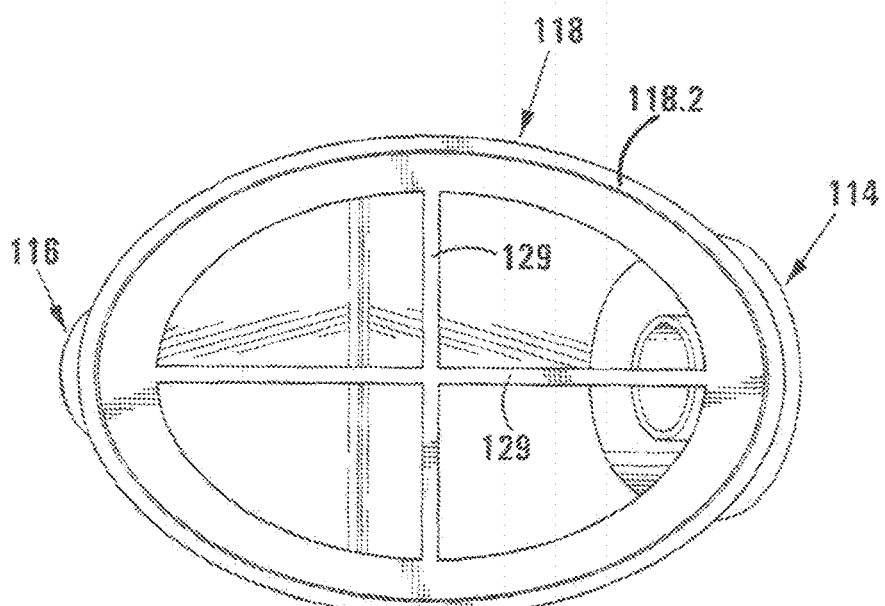
FIG. 12B also shows a bottom plan view of a body of the spacer device of the invention, which includes a cross-shaped filament extending across the interior cavity of the V-shaped body.
Figure 15:
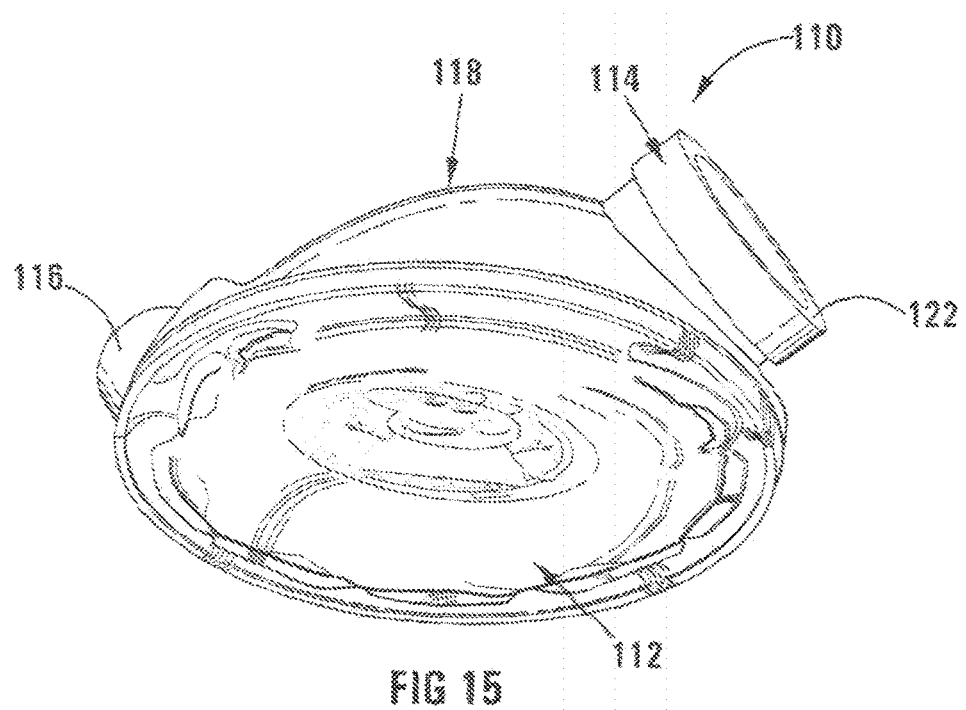
FIG. 15 shows a lower 3-D view of the spacer device in accordance with one aspect of the invention in which the bag is folded into the body of FIG. 12A for portability.
Figure 16:
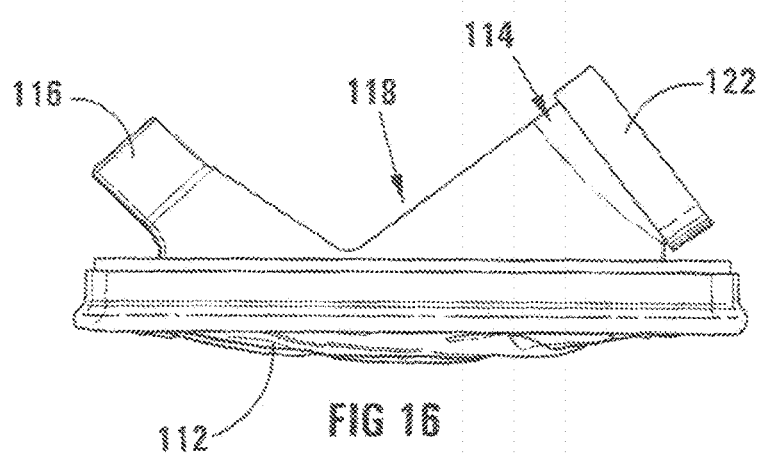
FIG. 16 shows a side view of the body with the bag stowed in the cavity as illustrated in FIG. 15.

As may be seen in FIGS. 12A and 12B, as well as in profile in FIGS. 13 and 14, the interior of the body 118 is V-shaped, commensurate with the outside of the body 118. The interior of the body 118 includes, in one embodiment, shown in FIG. 12B and FIG. 18, a cross-hair filament 129 that prevents the bag 112 from being sucked completely into the interior of the body 118, potentially blocking inlet 114 and outlet 116. However, testing has shown that the possibility of this occurring is slight and in the other embodiments shown the filament structure is omitted. FIGS. 15 and 16 show the inhaler spacer device 110 of the invention in which the bag 112 is nearly completely received or folded within the interior of the body for portability or transportation purposes. This serves to decrease the size and conspicuousness of the spacer device 110, making it easy to fit the spacer device 110 into a purse, handbag, or carry bag.

Figure 17:
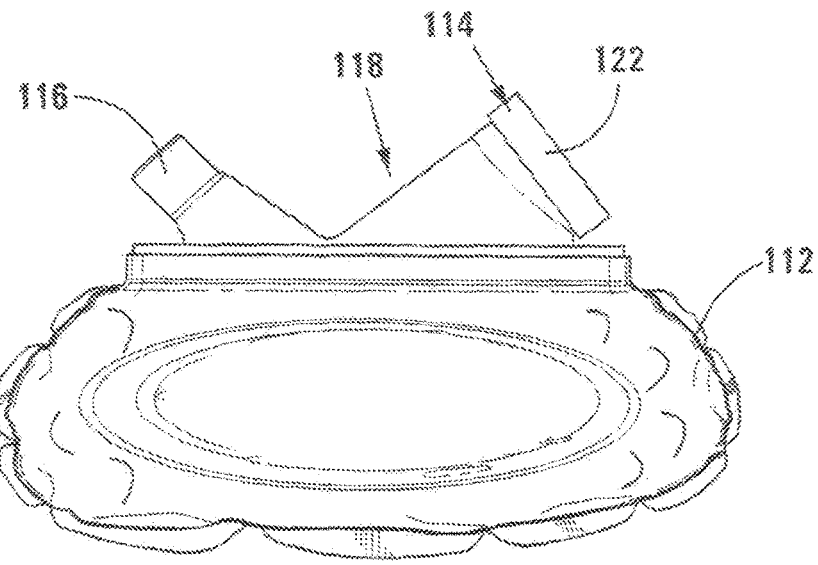
FIG. 17 shows a side view of a spacer device in accordance with one aspect of the invention in which a smaller bag is shown than in the previous embodiments.
Figure 18:
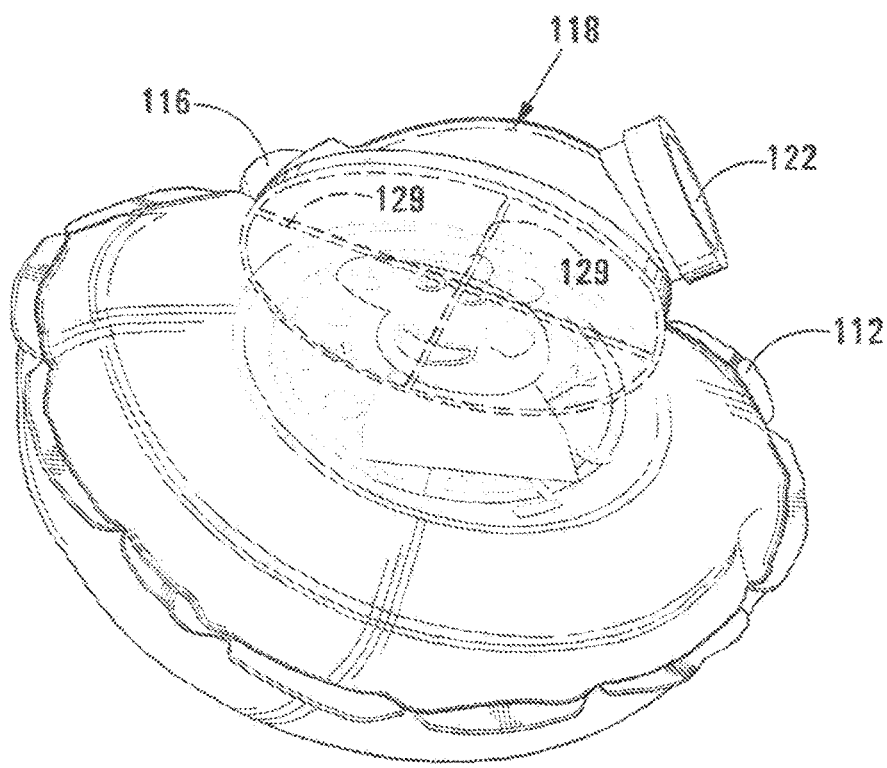
FIG. 18 shows a part cross-sectional lower 3-D view of a spacer device in accordance with one aspect of the invention.

As may be seen in FIG. 17, during inhalation, the bag 112 decreases in size only slightly in vertical cross-section, maintaining its vertical dimensions due to the resilience of seam 112.3 forming part of the bag 112. Inhalation thus generally results preferentially in the two opposing sides or "cheeks" 112.4, 112.5 (best seen in FIG. 10) of the bag 112 being drawn closer to each other, rather than the bag 112 being sucked into, and collapsing inwardly into the inner cavity of the body 118. The Applicant has found that even during sharp inhalation, not only the configuration and shape of the bag 112, (especially the shape-memory seam 112.3), but also the fact that the increase in negative pressure may reach a level where air is then entrained through the MDI attached to the mouthpiece and flows through the cavity of the base of the invention device, collectively prevent the bag from being sucked into the inner cavity defined by the housing 110 and potentially occluding the outlet 116.

Advantageously, a smaller bag may be used for children, the elderly, or those with compromised lung function (or to avoid conspicuousness), while larger bags may be used for adults.

The longitudinal axis (major axis) of the oval perimeter 118.1 in this embodiment is 9 cm. In another embodiment, this may be less (down to 2 cm, or less), or more (up to 20 cm, or more). The axis defining the maximum width (minor axis) of the oval perimeter 118.1 in this embodiment is 6.5 cm. In another embodiment, this may be less (down to 1 cm, or less) or more (up to 15 cm, or more). The ratio between the major axis and minor axis is typically 1.38:1.

The thickness of the wall of the V-shaped mounting can be adjusted for considerations relating to weight, strength, feel, and construction. In this embodiment, the wall is 2 mm thick through most of the mounting although this may vary. In other embodiments, this may be less, (down to 1 mm, or less) or more (up to 8 mm, or more).

The following experimental results indicate the effectiveness of the device of the invention.

Experiment 1

Aim: To compare the delivery efficiency of (i) a conventional large volume spacer, and (ii) the earlier spacer shown in FIGS. 1 to 9 of the current invention with a metalized collapsible chamber, using scintography and radio-labeled Fluticasone inhaled by a healthy adult.

Method: Single dose released from MDI in spacer followed by a single, deep, slow inhalation through the spacer, followed by a 10 second breath hold.

Outcomes:

Percentage of drug delivery to the lungs

Percentage of drug retained in spacer device

Distribution impression

Results:

Conventional Spacer:

30.46% of administered dose deposited in the lungs 19.7% retention of drug in the spacer.

Prominent throat deposition (i) Current Invention:

48.72% of administered dose deposited in the lungs

<1% retained in bag

Less throat deposition. Even lung distribution

Conclusions:

Using a single inhalation and 10-second breath hold, the current invention resulted in 18.26 percentage point increase in drug deposited (i.e. a 59% increase) in the lungs, with less throat deposition than a conventional spacer.

In addition, the conventional spacer retained 19.7% of drug in the device while the current invention retained <1% confirming superior emptying of drug from the device and detectable absence of retention effect caused by static electricity, or wall impaction, or both. There was also the impression of more even and peripheral lung deposition with the current device of the invention.

Experiment 2

Aim: To compare emitted dose from (i) conventional spacer, and (ii) the embodiment of the current invention shown in FIGS. 10 to 19, using a standard rebreathing simulator over 5 normal breaths, and also comparing the emitted dose direct from an MDI.

Methods:

Breathing simulator was connected to outlet (mouthpiece) of the spacer device

Set to simulate 5 normal adult breaths with tidal volume 500 ml and I:E ratio 1:2

Filter positioned at device outlet to capture all drug emitted from mouthpiece

One puff of Salbutamol (100 micrograms) delivered from MDI into spacer device.

Breathing simulator activated one second after actuation of MDI and drug expelled into spacer device.

Filter removed after 5 breaths and amount of Salbutamol deposited on filter measured by HPLC Finally, one puff from MDI deposited directly on to filter with no spacer in between Results:

Amount of Salbutamol recovered from filter:

MDI direct (no spacer)—67.6 micrograms

Current invention—61.7 micrograms

Conventional spacer—35.1 micrograms

Conclusion: The 5-breath rebreathing manoeuvre (recommended for small children and elderly patients) for a 100 microgram dose of Salbutamol, showed a 75% increase of medication delivered from the mouthpiece for the current invention spacer device compared to a conventional spacer device.

In the embodiment shown in FIGS. 10 to 18, this embodiment of the spacer device 110 of the invention allows the body 118 to be shortened to a desired length to suit the function and handling capability of the spacer device 110. This embodiment allows the chamber formed by bag 112 and body 118, by inflating and deflating below the body, to be less intrusive to the patient.

Usefully, the body (or "base") 118 and the bag 112—together defining chamber 120—can be separable allowing the bag 112 to be disconnected from the body 112. Amongst other indications, this disconnection may be indicated when a bag 112 is required to be cleaned or replaced when worn or contaminated, or simply replaced with one of a different size (volume) bag 112 depending on the need and capabilities of the patient.

The bag 112, when ready for use, spontaneously adopts a fully inflated position filled with air. The bag 112 is made of soft material providing negligible resistance to expansion and collapse making it capable of full deflation and re-inflation while the patient inhales and exhales during rebreathing. As mentioned hereinbefore, the bag 112 is metallised (typically made from a thin-section, easily collapsible polymeric metallised film such as Mylar®) such that it conducts electricity and therefore does not develop static electricity. The material thickness in one embodiment is 12.5 microns but is thinner (down to 5 microns or less) in another embodiment, or in a further embodiment, thicker (up to 25 microns, or more). The bag 112 can either collapse fully during inhalation allowing complete emptying of all the medication mist or droplets 127 originally expelled into the chamber 120 from the MDI in a single breath, or collapse partially (depending on the patient's breathing comfort and capabilities) allowing emptying to take place over a few breaths. The bag 120 can either re-expand fully or partially during exhalation to accommodate any unabsorbed medication 127. If during a deep exhalation the chamber 120 fills, the valveless inlet 114 will allow the excess air to escape through the MDI holder 156 (if necessary) thus avoiding any pressure build-up within the spacer device 110. Similarly, if the patient continues with a deep inhalation after the chamber 120 has emptied and collapsed completely, the casing around the MDI 156 will allow additional air to be entrained into the spacer device 110 and pass through the body 118 to the patient thus avoiding any limitation to inspiration.

The Applicant has identified the following advantages of the invention:

The low resistance to flow and easy collapsibility of the bag 112 provides the following advantages to patients:
1. No necessity for change of effort during breathing
2. No necessity for timing and co-ordination
3. No necessity for change to rate of breathing (number of breaths)
4. No necessity for change of flow (speed of inhalation and exhalation
5. No necessity to change the pattern of breathing (shallow or deep)

Furthermore, the Applicant has identified the following advantages associated with the invention. The metallic nature of the frame (body) 118 and bag 112 removes the potential for static electricity to cause particles to adhere to the interior walls and be retained in the spacer device 110. The bag 112 is detachable and comes in different volumes depending on medical need at the time and patient preference. The bag 112 is extremely pliant with extremely low resistance to inflation to full volume and deflation to empty or near-empty. The frame (body) 118 has an entrance end to which the MDI ("puffer") is connected and through which drug is expelled directly into the bag when the MDI is actuated. The angle of the entrance ensures that, following actuation of the MDI, the plume of the medication fans directly and in generally straight lines into the volume of the bag where the micro-dispersed droplets come to rest largely by their own inertia, thereby forming a reservoir cloud or mist of particles suspended in air and ready for inhalation.

In addition to the angle, the entrance being valveless ensures the particles contained in the spreading plume avoid or greatly lessens impaction against solid walls and surfaces, and come to rest in suspension in the cloud largely by their own inertia—a function not only of the entrance angles, but also dependent on the size of the bag.

During inhalation, the angle of the exit end (mouthpiece) and the absence of valves promotes unimpeded and laminar flow of the drug particles directly from the reservoir cloud in the bag through the mouthpiece into the mouth and then into the airway. The reservoir nature of the particles in the chamber (bag) allows the patient, when well and capable, to choose the desired flow rate and breath pattern for optimal lung deposition—ideally slow flow rate and deep inspiration. On the other hand, if the patient is unwell and unable to empty the chamber (bag) or adjust the breathing pattern, the valveless closed-circuit nature of the system will allow rebreathing which, over a few breaths, will empty any remaining drug from the chamber 120 by washout. During the exhalation phase of rebreathing, the angle of the outlet 116 once again favours unimpeded flow of exhaled air and any unabsorbed medication back into the volume of the bag, re-inflating the bag and re-forming the reservoir cloud that is then available for re-inhalation into the lung again. It is important to note that various types of extraneous mouthpieces (not shown) can be added to the outlet 116 depending on patient or condition requirements. This would include a face mask, if required.

The inferior positioning of the collapsible chamber 120 allows for a larger space (volume) to be used without significantly increasing intrusiveness to the patient. Larger volumes in chamber 120 are generally more efficient in drug delivery allowing better dispersal of drug particle droplets 127 and less inclination for impaction of drug particle droplets 127 on side walls. Current spacers of which the Applicant is aware have no flexibility regarding changing the volume of the spacer and essentially there are only two sizes of spacer chamber—small and large, The current invention offers easier emptying of larger volumes during single deep inhalation (low resistance to flow, no valve at outlet 116, collapsing bag 120 promoting emptying), and if emptying is not achievable in a single inhalation, then rebreathing will achieve this by washout with the valve-less, closed-circuit environment—usually within three to five breaths. If still not achievable, then switching to a smaller bag is a readily available option.

Essentially, the total amount of drug emitted from the MDI into the bag 112 is captured within the system and made available for unimpeded inhalation into the lungs either with single breath or rebreathing and with losses minimised at every step along the way. In addition, during use the amount of bag movement is an important indicator as to the amount of medication being inhaled. This provides accurate and important feedback and reassurance to the patient and/or observer and has been shown to be critical in promoting optimal use and adherence with treatment. No co-ordination or timing of inhalation in relation to actuation is required. Critically, the current invention device provides the user full control over flow rate at all times, and very low flow rates can be generated without compromising medication delivery—either using a single deep breath or multiple breaths such as during a simple tidal re-breathing manoeuvre. Low flow rates have been shown to minimize the amount of drug impacting and being retained in the mouth, pharynx and glottic area, while at the same time, ensuring that inhalant drug droplets or particles entering the airway are deposited more evenly through the lung, delivered to more peripheral parts of the lung, and penetrate better into diseased areas where they are needed most As such, the device of the invention, when compared to other inhalation devices, demonstrates:
 Improved efficiency of drug delivery to the airways;
 Static electricity as wall particle impaction leading to drug being retained in the device not being a significant issue;
 Reduced need for co-ordination between actuation and breathing;
 Improved ease of use, greater comfort and portability;
 Valuable visual and physiological feedback and reassurance to the patient regarding performance during the manoeuver
 Simplicity and low cost In addition, all these benefits are amplified in situations where achieving efficient drug delivery is usually most difficult, such as in very young or old patients, patients who are very ill (such as during a severe asthma attack), or in patients with chronic lung disease and damaged airways.

In final summary, the invention herein described utilizes the concept of an unvalved, low resistance, closed-circuit, rebreathing, anti-static, collapsible chamber to produce a device which allows a relaxed normal or low flow rate during inhalation and exhalation which is not dependent on co-ordination or any specific breathing pattern. These features are particularly beneficial when compared to current devices that the inventor is aware of, particularly when it comes to improved delivery efficiency, simplicity of use, and versatility.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

Figure 7:
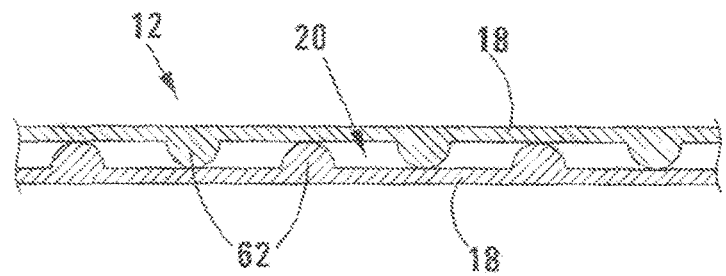
FIG. 7 is a partial sectional side view through an embodiment of the bag when deflated.

For, example the frame 50 can be integrally formed with the body 18 of the bag 12, whereby the rods are able to flex outwardly during inflation of the bag 12 but are not able to flex fully inwardly. Also, as shown in FIG. 7, the body 18 can be provided with numerous internal knobs or bulges 62 that are arranged to prevent the full collapsing of the bag 12.

Throughout this specification, unless the context requires otherwise, the word "comprise" or variations such as "comprises" or "comprising", will be understood to imply the inclusion of a stated integer or group of integers but not the exclusion of any other integer or group of integers.

Optional embodiments of the present invention may also be said to broadly consist in the parts, elements and features referred to or indicated herein, individually or collectively, in any or all combinations of two or more of the parts, elements or features, and wherein specific integers are mentioned herein which have known equivalents in the art to which the invention relates, such known equivalents are deemed to be incorporated herein as if individually set forth.

It is to be appreciated that reference to "one example" or "an example" of the invention is not made in an exclusive sense. Accordingly, one example may exemplify certain aspects of the invention, whilst other aspects are exemplified in a different example. These examples are intended to assist the skilled person in performing the invention and are not intended to limit the overall scope of the invention in any way unless the context clearly indicates otherwise.

It is to be understood that the terminology employed above is for the purpose of description and should not be regarded as limiting. The described embodiment is intended to be illustrative of the invention, without limiting the scope thereof. The invention is capable of being practised with various modifications and additions as will readily occur to those skilled in the art.

Various substantially and specifically practical and useful exemplary embodiments of the claimed subject matter are described herein, textually and/or graphically, including the best mode, if any, known to the inventors for carrying out the claimed subject matter. Variations (e.g. modifications and/or enhancements) of one or more embodiments described herein might become apparent to those of ordinary skill in the art upon reading this application.

The inventor(s) expects skilled artisans to employ such variations as appropriate, and the inventor(s) intends for the claimed subject matter to be practiced other than as specifically described herein. Accordingly, as permitted by law, the claimed subject matter includes and covers all equivalents of the claimed subject matter and all improvements to the claimed subject matter. Moreover, every combination of the above described elements, activities, and all possible variations thereof are encompassed by the claimed subject matter unless otherwise clearly indicated herein, clearly and specifically disclaimed, or otherwise clearly contradicted by context.

The use of any and all examples, or exemplary language (e.g., "such as") provided herein, is intended merely to better illuminate one or more embodiments and does not pose a limitation on the scope of any claimed subject matter unless otherwise stated. No language in the specification should be construed as indicating any non-claimed subject matter as essential to the practice of the claimed subject matter.

The use of words that indicate orientation or direction of travel is not to be considered limiting. Thus, words such as "front", "back", "rear", "side", "up", "down", "upper", "lower", "top", "bottom", "forwards", "backwards", "towards", "distal", "proximal", "in", "out" and synonyms, antonyms and derivatives thereof have been selected for convenience only, unless the context indicates otherwise. The inventor(s) envisage that various exemplary embodiments of the claimed subject matter can be supplied in any particular orientation and the claimed subject matter is intended to include such orientations.

The use of the terms "a", "an", "said", "the", and/or similar referents in the context of describing various embodiments (especially in the context of the claimed subject matter) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted.

Moreover, when any number or range is described herein, unless clearly stated otherwise, that number or range is approximate. For example, if a range of 1 to 10 is described, that range includes all values there between, such as for example, 1.1, 2.5, 3.335, 5, 6.179, 8.9999, etc., and includes all sub-ranges there between, such as for example, 1 to 3.65, 2.8 to 8.14, 1.93 to 9, etc.

Accordingly, every portion (e.g., title, field, background, summary, description, abstract, drawing figure, etc.) of this application, other than the claims themselves, is to be regarded as illustrative in nature, and not as restrictive; and the scope of subject matter protected by any patent that issues based on this application is defined only by the claims of that patent.

The invention claimed is:

1. A valveless spacer device for a metered dose inhaler (MDI), the spacer device comprising:
   a body having an inlet and an outlet opposed from the inlet;
   a demountable, flexible bag attached to the body, the bag and body together defining a chamber, such that the inlet and outlet are in fluid flow communication with an interior of the chamber;
   wherein the inlet is configured to be connected to the MDI containing a drug to be inhaled;
   wherein the outlet is configured to be received by a user's mouth;
   wherein the flexible bag is configured to serve as a reservoir following actuation of the MDI, the reservoir configured to allow for the formation of a cloud or mist of the drug therewithin which is then ready for inhalation, the flexible bag being configured to be at least partially deflatable and at least partially inflatable commensurate with a single breath and/or rebreathing;

wherein the inlet comprises a mount defining an inlet passage for sealingly engaging with a mouthpiece of the MDI and the outlet comprises a mouthpiece defining an outlet passage;

wherein the body is in the form of a generally V-shaped mounting which is formed by the inlet passage and the outlet passage intersecting at an angle along their respective longitudinal axes; and wherein the V-shaped mounting includes a V-shaped interior surface, shaped and dimensioned to define a cavity that provides a passage for flow of air and/or medication between the inlet and the bag and between the bag and the outlet and has a lower perimeter formed by a merging of inferior and lateral aspects of the inlet and outlet, the lower perimeter comprising the portion of the V-shaped mounting that receives the demountable bag.

2. The spacer device of claim 1, wherein any one or more of the body, inlet, bag or outlet are configured to reduce a static electricity charge by being treated with an antistatic agent or being made of electrically conductive material.

3. The spacer device of claim 1, wherein the bag is made of a metallised film or aluminium foil.

4. The spacer device of claim 1, wherein the body is external to the bag and the bag depends operatively downwardly, as directed by gravity, from a base, and wherein the base is a portion of the body to which the bag is attached.

5. The spacer device of claim 1, wherein the lower perimeter is generally oval in shape.

6. The spacer device of claim 5, wherein the interior of the V-shaped mounting is sized, shaped, and dimensioned to receive the bag, when the bag is folded into the cavity for portability.

7. The spacer device of claim 1, wherein the bag has an opening including a peripheral collar that is shaped and dimensioned to fit securely to lower perimeter of the body of the spacer device, thereby to releasably attach the bag to the body of the spacer device.

8. The spacer device of claim 7, wherein the collar extends along an upper periphery of the bag opening oriented away from a body of the bag, and extends at least partially around the opening of the bag.

9. The spacer device of claim 7, wherein the bag opening is biased towards an open, distended position and wherein the collar is a resiliently flexible material, and wherein the bag is configured to spontaneously adopt an open, inflated position prior to use.

10. The spacer device of claim 7, wherein the bag has shape or material memory to allow it to retain an open inflated position.

11. The spacer device of claim 7, wherein the bag is provided with a peripherally extending, resiliently flexible seam to resist vertical collapse of the bag relative to the body.

12. The spacer device of claim 7, wherein the collar is made of a resiliently flexible material that urges the collar against an outer surface of the lower perimeter of the body.

13. The spacer device of claim 7, wherein the collar is shaped and dimensioned to encircle and attach in a friction-fit or snap-fit manner to the lower perimeter of the body.

14. The spacer device of claim 7, wherein the collar comprises a threaded collar that engages with a complementarily threaded portion of the lower perimeter of the body.

* * * * *